United States Patent [19]

Hutchison

[11] Patent Number: 4,918,745
[45] Date of Patent: Apr. 17, 1990

[54] MULTI-CHANNEL COCHLEAR IMPLANT SYSTEM

[75] Inventor: Steve Hutchison, Kirkwood, Mo.

[73] Assignee: Storz Instrument Company, St. Louis, Mo.

[21] Appl. No.: 106,571

[22] Filed: Oct. 9, 1987

[51] Int. Cl.⁴ .......................... H04B 5/00; A61N 1/00
[52] U.S. Cl. ....................................... 455/41; 379/52;
              379/55; 128/784; 128/420.5
[58] Field of Search ................. 455/41, 129, 121, 108;
         128/419 PT, 784, 789, 420.5, 420.6; 333/108 A;
                                     379/52, 55; 375/111

[56] References Cited

U.S. PATENT DOCUMENTS

| | | |
|---|---|---|
| Re. 31,031 | 9/1982 | Kissiah, Jr. . |
| 681,341 | 8/1901 | Payn, Jr. . |
| 2,164,121 | 6/1939 | Pescador . |
| 2,995,633 | 8/1961 | Puharich et al. . |
| 3,170,993 | 2/1965 | Puharich et al. . |
| 3,195,540 | 7/1965 | Waller . |
| 3,209,081 | 9/1965 | Ducote et al. . |
| 3,267,931 | 8/1966 | Puharich et al. . |
| 3,311,111 | 3/1967 | Bowers . |
| 3,393,279 | 7/1968 | Flanagan . |
| 3,449,768 | 6/1969 | Doyle . |
| 3,493,695 | 2/1970 | Stork . |
| 3,518,997 | 7/1970 | Sessions . |
| 3,649,742 | 3/1972 | Tissot . |
| 3,672,352 | 6/1972 | Summers . |
| 3,751,605 | 8/1973 | Michelson . |
| 3,752,939 | 8/1973 | Bartz . |
| 3,808,577 | 4/1974 | Mathauser . |
| 3,841,306 | 10/1974 | Hallgren . |
| 3,989,904 | 11/1976 | Rohrer et al. . |
| 4,024,855 | 5/1977 | Bucalo . |
| 4,025,732 | 5/1977 | Traunmuller . |
| 4,025,964 | 5/1977 | Owens . |
| 4,063,048 | 12/1977 | Kissiah, Jr. . |
| 4,099,035 | 7/1978 | Yanick . |
| 4,112,941 | 9/1978 | Larimore . |
| 4,284,856 | 8/1981 | Hochmair et al. . |
| 4,289,935 | 9/1981 | Zollner et al. . |
| 4,340,038 | 7/1982 | McKean . |
| 4,352,960 | 10/1982 | Dermer et al. . |
| 4,357,497 | 11/1982 | Hochmair et al. . |
| 4,366,349 | 12/1982 | Adelman . |
| 4,396,806 | 8/1983 | Anderson . |
| 4,400,590 | 8/1983 | Michelson . |
| 4,403,118 | 9/1983 | Zollner et al. . |
| 4,408,608 | 10/1983 | Daly et al. . |
| 4,419,544 | 12/1983 | Adelman . |
| 4,419,995 | 12/1983 | Hochmair et al. . |
| 4,425,481 | 1/1984 | Mansgold et al. . |
| 4,428,377 | 1/1984 | Zollner et al. . |
| 4,441,202 | 4/1984 | Tong et al. . |
| 4,441,210 | 4/1984 | Hochmair et al. ..................... 455/41 |
| 4,471,171 | 9/1984 | Kopke et al. . |
| 4,484,345 | 11/1984 | Stearns . |
| 4,491,793 | 1/1985 | Germer et al. . |
| 4,495,384 | 1/1985 | Scott et al. . |
| 4,516,820 | 5/1985 | Kuzma . |
| 4,654,880 | 3/1987 | Sontag ................................... 455/41 |

FOREIGN PATENT DOCUMENTS

| | | |
|---|---|---|
| 2823798 | 5/1978 | Fed. Rep. of Germany . |
| 2403084 | 9/1977 | France . |
| 2124495 | 2/1984 | United Kingdom . |

OTHER PUBLICATIONS

K. J. Dormer, Ph.D. et al., "The Cochlear Implant (Auditory Prosthesis) Utilizing Rare Earth Magnets", American Journal of Otology, vol. 2, No. 1, pp. 22–27, 7/1980.

K. J. Dormer et al., "The Use of Rare-Earth Magnet Couplers in Cochlear Implants", The Laryngoscope, vol. XCI, No. 11, pp. 1812–1820, 11/1981.

(List continued on next page.)

*Primary Examiner*—Robert L. Griffin
*Assistant Examiner*—Ralph Smith
*Attorney, Agent, or Firm*—Brooks & Kushman

[57] ABSTRACT

A method and system is described for electrically stimulating the auditory nerve with multiple channels of audio information. Audio information is transmitted from an external microphone to a speech processor through a single transcutaneous path to an implanted receiving device. Power is transmitted through a second transcutaneous path to power the implanted device.

22 Claims, 6 Drawing Sheets

OTHER PUBLICATIONS

Wolf D. Keidel, "Neurophysiological Requirements for Implanted Cochlear Prostheses", *Acta Otolaryngol*, vol. 87, Nos. 3-4, pp. 163-169, 3/1979.

F. B. Simmons et al., "A Functioning Multichannel Auditory Nerve Stimulator", *Acta Otolaryngol*, vol. 87, Nos. 3-4, pp. 170-175, 3/1979.

W. F. House et al., "Present Status and Future Directions of the Ear Research Institute Cochlear Implant Program", *Acta Otolaryngol*, vol. 87, Nos. 3-4, pp. 176-184, 3/1979.

P. Pialoux et al., "Indications and Results of the Multichannel Cochlear Implant", *Acta Otolaryngol*, vol. 87, Nos. 3-4, pp. 185-189, 3/1979.

K. Burian et al., "Designing of and Experience with Multichannel Cochlear Implants", *Acta Otolaryngol*, vol. 87, Nos. 3-4, pp. 190-195, 3/1979.

M. M. Merzenich et al., "Some Considerations of Multichannel Electrical Stimulation of the Auditory Nerve in the Profoundly Deaf; Interfacing Electrode Arrays with the Auditory Nerve Array", *Acta Otolaryngol*, vol. 87, Nos. 3-4, pp. 196-203, 3/1979.

N. Y. S. Kiang et al., "Fundamental Considerations in Designing Auditory Implants", *Acta Otolaryngol*, vol. 87, Nos. 3-4, pp. 204-218, 3/1979.

W. F. House, M.D, "Cochlear Implants", *The Annals of Otology, Rhinology & Laryngology*, vol. 85, No. 3, Part 2, Supplement 27, pp. 1-93, 5/1976.

Hochmair-Desoyer et al., "Design and Fabrication of Multiwire Scala Tympani Electrodes", Annals New York Academy of Sciences, pp. 173-182, 1983.

E. Hochmair et al., "Process for the Electrical Stimulation of the Auditory Nerve & Multichannel Hearing Prosthesis for Carrying Out the Process", West German Pub. No. 28 23 798, App. Date 5/31/78, pp. 1-30, 9/13/79.

M. Merzenich, "Cochlear Prostheses—An International Symposium—Coding of Sound in a Cochlear Prosthesis: Some Theoretical & Practical Considerations", *Annals New York Academy of Sciences*, vol. 405, pp. 502-508, 1983.

R. P. Michelson et al., "A Cochlear Prosthesis: Further Clinical Observations; Preliminary Results of Physiological Studies", The Laryngoscope, vol. LXXXIII, No. 7, pp. 1116-1122, 7/1973.

M. Merzenich et al., "Neural Encoding of Sound Sensation Evoked by Electrical Stimulation of the Acoustic Nerve", *Annals of Otology, Rhinology & Laryngology*, vol. 82, No. 4, p. 486, 7/1973.

M. Merzenich et al., "Representation of the Cochlea Within the Inferior Colliculus of the Cat", *Brain Research*, vol. 77, pp. 397-415, 1974.

R. P. Michelson, "The Results of Electrical Stimulation of the Cochlea in Human Sensory Deafness", *Annals of Otology, Rhinology & Laryngology*, vol. 80, No. 6, p. 914, 12/1971.

R. P. Michelson, "Electrical Stimulation of the Human Cochlea", *Arch Otolaryng*, vol. 93, pp. 317-323, 3/1971.

M. Merzenich et al., "Symposium on Cochlear Implants. II. Feasibility of Multichannel Scala Tympani Stimulation", *The Laryngoscope*, vol. LXXXIV, No. 11, pp. 1887-1893, 11/1974.

G. E. Loeb et al., "Design & Fabrication of an Experimental Cochlear Prosthesis", *Medical & Biological Engineering & Computing*, vol. 21, pp. 241-254, 5/1983.

G. E. Leob, "The Functional Replacement of the Ear", *Scientific American*, pp. 104-111.

M. W. White et al., "Multichannel Cochlear Implants", *Archives of Otolaryngology*, vol. 110, pp. 493-501, 8/1984.

B. J. Gantz et al., Technical Paper, "Initial Results with Two Single-Channel Cochlear Implants", University of Iowa, Dept. of Otolarynology-Head & Neck Surgery.

Richard Layne, "Biomechanical Ear Brings Hearing to Deaf", *Popular Science*, p. 40, 10/1985.

M. Merzenich et al., "Cochlear Implant—The Interface Problem", *Biomedical Engineering & Instrumentation Functional Electrical Stimulation*, vol. 3, pp. 321-340, 1977.

David Perlman, "Implant Developed at UC, Hearing Device for the Totally Deaf", *San Francisco Chronicle*, p. 3, 3/8/85.

Storz Instrument Co., SPA-1238, Brochure, "An Introduction to the Cochlear Implant", U of C, San Francisco School of Medicine and Storz Instrument Co.

J. F. Patrick et al., "Australian Multi-Channel Implantable Hearing Prosthesis", *Cochlear Implants*, pp. 93-100, 1985.

Michael J. Danley et al., Technical Paper, "Design and Functioning of the Single-Electrode Cochlear Implant", pp. 21-26.

Kenneth K. Clarke et al., "Communication Circuits: Analysis and Design", Addison-Wesley Publishing Co., title page.

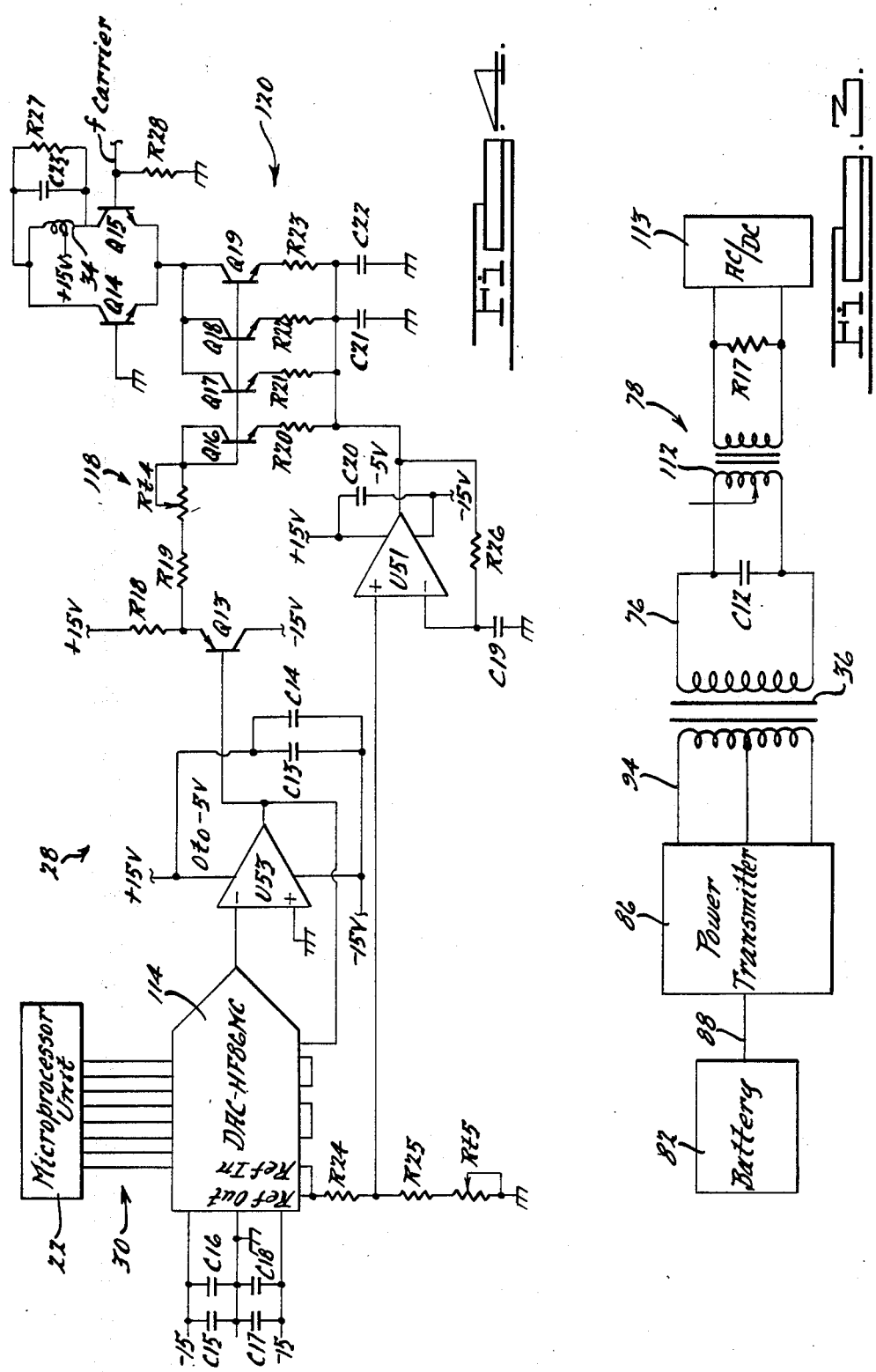

MULTI-CHANNEL COCHLEAR IMPLANT SYSTEM

BACKGROUND OF THE INVENTION

The present invention relates generally to a cochlear implant auditory prosthesis, and particularly to a multichannel cochlear implant system which transmits speech information and electrical power across separate transcutaneous paths.

In recent years, a method has been developed for inducing the sensation of hearing in people suffering from sensory deafness. This method involves the direct electrical excitation of the auditory nerve endings distributed along the basilar membrane of the cochlea of the ear. The electrical stimulus is generated by an auditory prosthesis known as the cochlear implant. Cochlear implants generally comprise at least one antenna coil, a receiver, and an electrode. The antenna coil is used to receive radio frequency transmitted signals representing sould from an external inductive coil assembly disposed over the implanted antenna coil. The receiver then detects or demodulates the electrical signal sent by the antenna coil. This processed electrical signal is then transmitted to the electrode which creates an electrical field along the basilar membrane within the cochlea or otherwise distributes the processed signal along this membrane.

In some cochlear implant designs, a single communications channel is established between the external transmitter and the subcutaneous receiver of the cochlear implant. In these systems, one antenna coil receives the radio frequency transmitted sound excitation signal. While in other cochlear implant designs, multiple communication channels are established between the transmitter and the receiver. Multiple channel cochlear systems usually utilize one antenna coil for each of the communication channels.

A further discussion of cochlear implants may be found in the following patents: U.S. Pat. No. 3,751,605, issued on Aug. 7, 1973 to Robin P. Michelson; U.S. Pat. No. 3,752,939 issued on Aug. 14, 1973 to Melvin C. Bartz; U.S. Pat. No. 4,495,917, issued on Jan. 29, 1985 to Charles L. Byers; U.S. Pat. No. 4,400,590, issued Aug. 23, 1983 to Robin P. Michelson. Additional discussions of cochlear implants may also be found in to following publication: "The Functional Replacement of the Ear" by Gerald E. Loeb, *Scientific American,* Vol. 252, No. 2, dated 2/9/85, pp. 104–111; "Design and Fabrication of an Experimental Cochlear Prosthesis" by Gerald E. Loeb, et al. May 1983, pp. 241–254, *Medical and Biological Engineering and Computing.* The above identified patents and publications are incorporated herein by reference.

Multiple channel cochlear implant systems are believed to be preferable to single channel systems as a result of the place-pitch theory. In accordance with this theory, the pitch of the sound perceived when the cochlea is stimulated depends upon which portion of the basilar membrane within the cochlea is stimulated. When the base of the cochlea is stimulated, higher pitches are perceived. As the stimulus moves toward the apex of the cochlea, the perceived pitch lowers. It will be appreciated that it is difficult for a single channel system to stimulate discrete protions of the cochlea and thereby stimulate the preception of different pitches. Indeed, some experiments have shown that a minimum of six separate channels of stimulation are necessary to create enough pitch discrimination to simulate intelligible speech.

The number of channels in a cochlear implant system is limited by a number of factors. One limitation is the number of electrodes. Implanted electrodes must be spaced a sufficient distance apart to prevent interaction between adjacent electrode contacts. Because of this, current implants often employ bipolar electrode contacts which provide a more localized pattern of excitation. The size and shape of the cochlea also limits the number of electrodes which may be implanted.

The numbers of channels in a cochlear implant system is also limited by the method employed to transmit electrical signals across the skin. In present multi-channel cochlear implant systems, a separate transmitter/receiver antenna pair is usually employed for transmitting each communication channel. Thus, for example, in the article "The Functional Replacement of the Ear" referred to above, four transmitter/receiver antenna pairs are shown—one for each channel in the cochlear implant design. While this approach is appropriate for cochlear implants with relatively few channels, this approach is difficult to implement for cochlear implants employing six or more channels. This is because the size of the coils places a practical limit on the number of coils that can be attached on both sides of the patient's skin.

Thus, it would be desirable to provide a multi-channel cochlear implant system which requires few or even just one antenna/receiver pair for transmitting all of the channels of information. A significant problem, however, in such a system, would be the increase in the complexity of the signal processing circuitry that would be required by the implanted receiver circuit. This creates difficulties due to the size and power limitations on the implanted device. The power required to drive both the implanted circuitry and the electrodes could necessitate the use of an implanted battery. Such a battery is undesirable because it requires additional space and must be replaced periodically.

Moreover, supplying electrical power to the implant is difficult even in conventional implant designs. A relatively large amount of electrical power is required to drive the implanted electrodes. In conventional cochlear implants often both the audio signal and electrical power are transmitted across a single antenna coil pair. While a wide bandwidth is necessary for effective transmission of the audio signal, this results in large power losses across the cutaneous layer. As a result, not much of the transmitted power is available to drive the electrodes. This sometimes results in excessive drain on the external battery worn by the user. It will be appreciated that a narrow bandwidth signal would be more efficient for transmitting electrical power across the skin. Thus, it would be desirable to provide a multi-channel cochlear implant system which transmits electrical power across a separate antenna using a narrow bandwidth signal.

Besides improving pitch discrimination, having multiple channels allows greater flexibility in modifying the electrical stimulation to improve the perception of speech in the patient. This is because in some patients, portions of the cochlea do not respond to electrical stimulation. Also, malfunctions can occur which limit the functioning of a particular electrode. Thus, for example, in a four channel implant system one or more channels may become non-functional. The conventional approach in such a case would be to combine the audio signals from the non-functioning channel with the signals for the functioning channel. In this way, the full audio spectrum is retained. This results, however, in a reduction in the number of discrete channels of stimulation to three or less. Thus, it would be desirable to provide a cochlear implant with a large number of electrodes so that a greater number of functioning electrodes remain if some of the electrodes become non-functional.

Also, prior multiple channel cochlear implants have generally employed a fixed filtering and processing scheme to divide the full spectrum of audio frequencies into discrete channels to stimulate the individual monopolar or bipolar electrodes. However, since a patients' response to cochlear implants may vary widely, some patients may achieve better results with monopolar instead of bipolar electrodes. This is because the nerve damage in some implant patients may differ in its location and severity in comparison with other implant patients.

Therefore, it would thus be desirable to provide a programmable multi-channel cochlear implant system in which various audio and auditory parameters can be easily optimized after the implant is in place. These parameters include changing from a monopolar to a bipolar electrode configuration, changing the content of each channel with respect to the frequency, changing the bandwidth and phase of the signal, and compensating for non-functioning electrodes. For example, a programmable multi-channel implant would be able to manipulate the incoming signal to the implant in new ways. The patient then could be expected to achieve greater comprehension of speech than was previously possible. An added benefit of such a system would be its utility as a research tool to advance our understanding of the auditory system and thereby further the development of future auditory prosthesis systems.

Accordingly, it is a principal objective of the present invention to provide a multi-channel cochlear implant system which transmits multiple channels of audio information across a single wireless transcutaneous path to produce intelligible perception of speech. It is also a principal objective to provide a multi-channel cochlear implant system which efficiently transmits electrical power to the implant across a separate wireless transcutaneous path so that excessive current is not drawn from the external battery.

It is another objective of the present invention to provide a portable cochlear implant system which has relatively low power requirements, and permits the transmission of speech information over a wide bandwidth and also permits the transmission of electrical power over a narrow bandwidth.

It is also an object of the present invention to provide a programmable multi-channel cochlear implant system in which the audio information contained in each channel can be easily altered after the implant is in place, to tailor the electrical stimulation to the patient's individual needs, and thereby optimize the comprehension of speech.

It is an additional objective of the present invention to provide an implantable receiver circuit which can synchronize itself with the transmitted channels of speech data and also transmit these channels of data to individual implanted cochlear electrodes in a predetermined sequence.

It is also an objective of the present invention to provide a system which can transmit electrical power across the skin to an implanted circuit and to also adjust the frequency of the transmitted signal to optimize the efficiency of the power transmission.

SUMMARY OF THE INVENTION

In order to achieve the foregoing objectives, the present invention provides a multi-channel cochlear implant system which utilizes one external antenna coil to transmit multiple channels of speech/audio information and another external coil to transmit electrical power. Also one internal coil is used to receive the multiple channels of speech/audio information and another internal coil is used to receive electrical power.

In one embodiment according to the present invention, speech/audio signals are converted into sixteen multiple channels of speech/audio data by a speech processor. This data is converted into a wide bandwidth amplitude modulated AC signal which is transmitted from the external coil across the skin to an internal coil. An internal envelope detector circuit then rectifies this AC signal. A synchronization detector circuit and a phase comparator circuit adjust the delay of the rectified signal until the clock pulse of the internal and external circuits are synchronized. A ring counter circuit then sequentially directs the sixteen separate channels of data to sixteen driver circuits. The drivers amplify each signal before sending it to each of the implanted electrodes.

In one embodiment of the present invention, to provide the implant system with electrical power, a power transmission circuit converts DC current from an external battery into an alternating current power signal. The frequency of this power signal is adjusted by a voltage controlled oscillator circuit which is controlled by a microprocessor. The microprocessor senses the electrical current drawn from the battery and adjusts the frequency of the power signal to minimize this current. This process maximizes the efficiency of power transmission across the skin.

Additional advantages and features of the present invention will become apparent from the detailed description of the preferred embodiment which makes reference to the following set of drawings.

BRIEF DESCRIPTION OF THE DRAWINGS

FIG. 3 is a circuit diagram of the power receiver circuit shown in FIG. 1.

FIG. 4 is a circuit diagram of the speech signal transmitter shown in FIG. 1.

DETAILED DESCRIPTION OF THE PREFERRED EMBODIMENT

Figure 1:
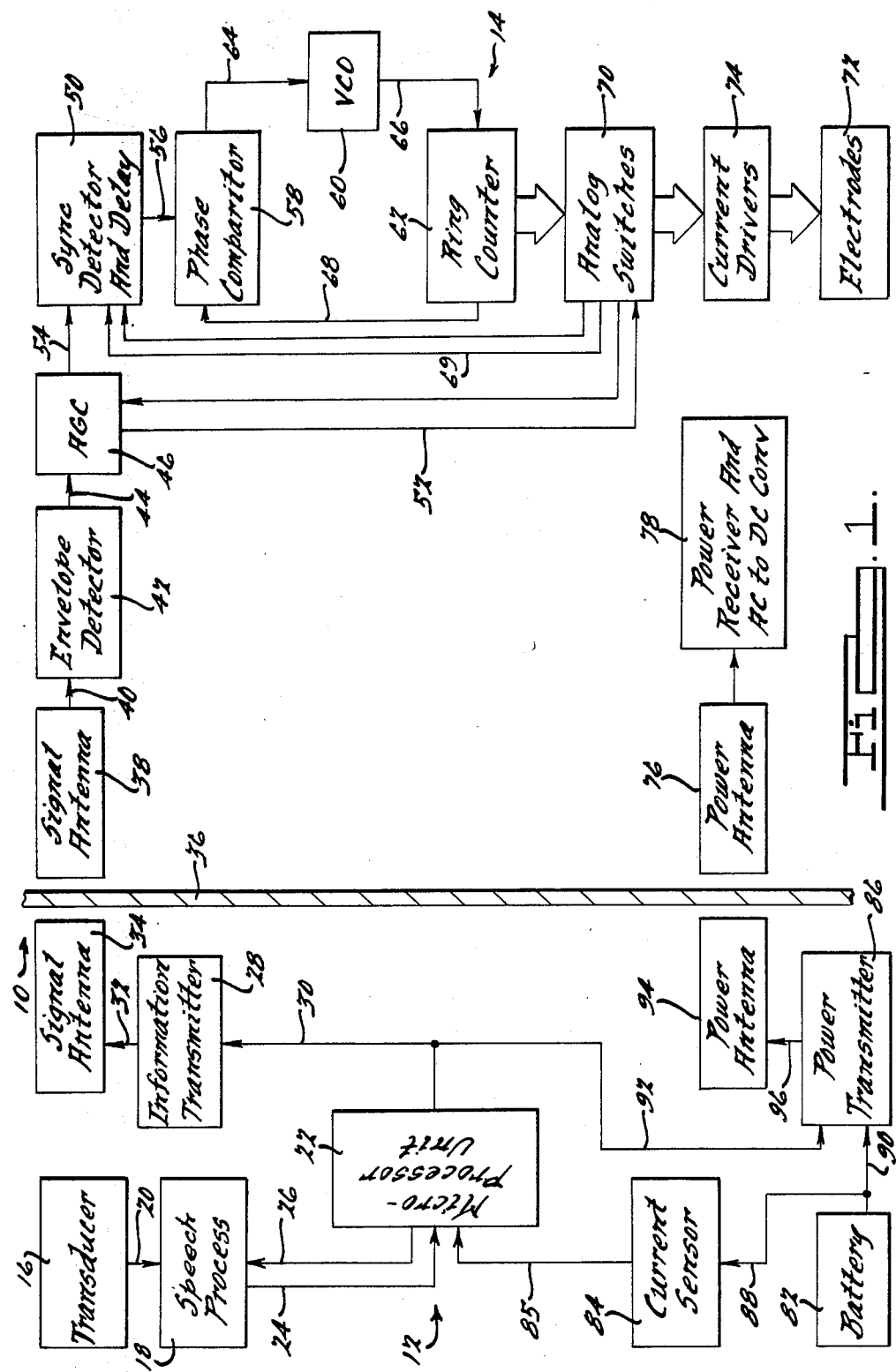
FIG. 1 is a block diagram of a multi-channel cochlear implant system according to the present invention.

Referring to FIG. 1, a block diagram of a cochlear implant system 10 according to the present invention is shown. The system includes an external module 12, which may be worn by the person receiving the implant, and an implant module 14, which is surgically implanted in the patient.

The external module 12 includes a transducer 16 which creates an electrical signal in response to an external audio stimulus. The audio stimulus may include various kinds of sounds including human speech. The transducer 16 is connected to a speech processor 18 by a conductor 20.

As will be appreciated by those skilled in the art, a speech or audio processor is a device which can create multiple channels of speech or audio information in response to an electrical signal from a microphone. Such speech processors are described in various prior art cochlear implant systems. See, for example, U.S. Pat. No. 4,400,590 issued on Aug. 23, 1983 to Robin R. Michelson. The output of the speech processor may consist of various channels of audio information. Each channel may contain a predetermined portion of the audio frequency spectrum.

In one embodiment according to the present invention, the speech processor 18 will have controls to allow the user to adjust the gain, volume and frequency range of the signals. In this embodiment, it will also produce eight to sixteen channels of speech information. Speech information is then fed to a microprocessor 22, through a conductor 24. The microprocessor 22 can be programmed to control the operation of the speech processor 18 through a conductor 26 and thereby determine the resulting sequence and content of each channel of speech information.

In one embodiment according to the present invention, the speech processor 18 contains an analog to digital converter. It is necessary that analog information be converted into digital information before the microprocessor can manipulate this signal. In another embodiment, the microprocessor 22 may also contain a speech processor so that both functions are performed by a single device.

Multiple channels of digital speech information are then fed from the microprocessor 22 into an information transmitter circuit 28 through a conductor 30. The information transmitter circuit 28 converts the digital signal back into an analog signal and then converts this analog signal into a wide bandwidth amplitude modulated sine wave signal. This signal is then sent along a conductor 32 to a signal antenna coil 34. In one embodiment according to the present invention, this signal contains clock and synchronization (synch) pulses. The sync pulse occurs during every seventeenth and eighteenth clock cycle; during this time no information is being sent. Audio information is sent during approximately fifty percent of each of the clock cycles, one through sixteen. This duty cycle may be varied, but the fifty percent value is preferred since it minimizes crosstalk between channels while still achieving a desired band width. While this embodiment employs an analog signal for transcutaneous transmission, it should be appreciated that other types of signals may be employed in the appropriate application.

In accordance with the method of the present invention, the signal is then transmitted by the antenna coil 34 across the cutaneous layer 36 and is magnetically coupled to an implanted antenna coil 38. However, other means of coupling the external circuitry with the implanted circuitry may be employed in the appropriate application, such as infrared light, capacitance, electromagnetic or radio frequency coupling.

The implanted antenna coil 38 is connected through conductor 40 to an envelope detector 42 which rectifies the AC speech/audio signal. In one embodiment according to the present invention, the rectified signal is sent along conductor 44 to an automatic gain control (AGC) circuit 46. Such an automatic gain control circuit 46 may be employed to ensure that the signal amplitude remains below a predetermined maximum value. The AGC circuit may also control the synchronization level. The signal is then sent from the automatic gain control circuit 46 to a set of analog switches 48 and to a sync detector circuit 50 by means of conductors 52 and 54.

The sync detector circuit 50 senses the sync signals present in the seventeenth and eighteenth channels of speech/audio information transmitted to the implant module 14. The detected sync signal is then sent along conductor 56 to a phase comparator 58 which is in a loop configuration with a voltage controlled oscillator 60 and a ring counter 62 by means of conductors 64, 66 and 68. The ring counter 62 controls the flow of the multi-channel audio signal into analog switches 70. The analog switches are each connected to one of the electrodes 72 through one of the current drivers 74.

The result of the above circuit is that the timing of the clock and sync pulses are adjusted until the internal and external circuits of the cochlear implant 10 are synchronized. This ensures that each of the analog switches 70 is turned on at precisely the time that the audio signal for that channel is to be optimally transmitted to the appropriate electrode.

Before the audio signal is sent to the proper electrode, it should be current amplified with an estimated compliance voltage of between $\pm 15$ to $\pm 20$. This amplification is performed by one or more of the current drivers 74. The voltage supplied to the current drivers 74 is provided from a power receiver circuit 78 and to the rest of the receiver circuitry.

Electrical power for the implant system 10 originates at a battery 82 which is contained in the external module 12. The battery 82 is connected to a current sensor 84 and to a power transmitter circuit 86 by means of two conductors 88 and 90. The current sensor 84 is coupled to the microprocessor 22 by means of conductor 85. The microprocessor 22 responds to the current measured by the current sensor 84, and sends a signal along conductor 92 which detects the power transmitter 86 to raise or lower the frequency of a power transmission signal to the implant module 14. In this way, the current drawn from the battery is minimized because the efficiency of the power transmission is optimized. The power transmitter 86 generates a narrow bandwidth signal which is then transmitted to a power antenna coil 94 along conductor 96. The power antenna coil 94 then transmits this signal across the cutaneous layer 36 to the implanted power antenna coil 76.

Figure 2:
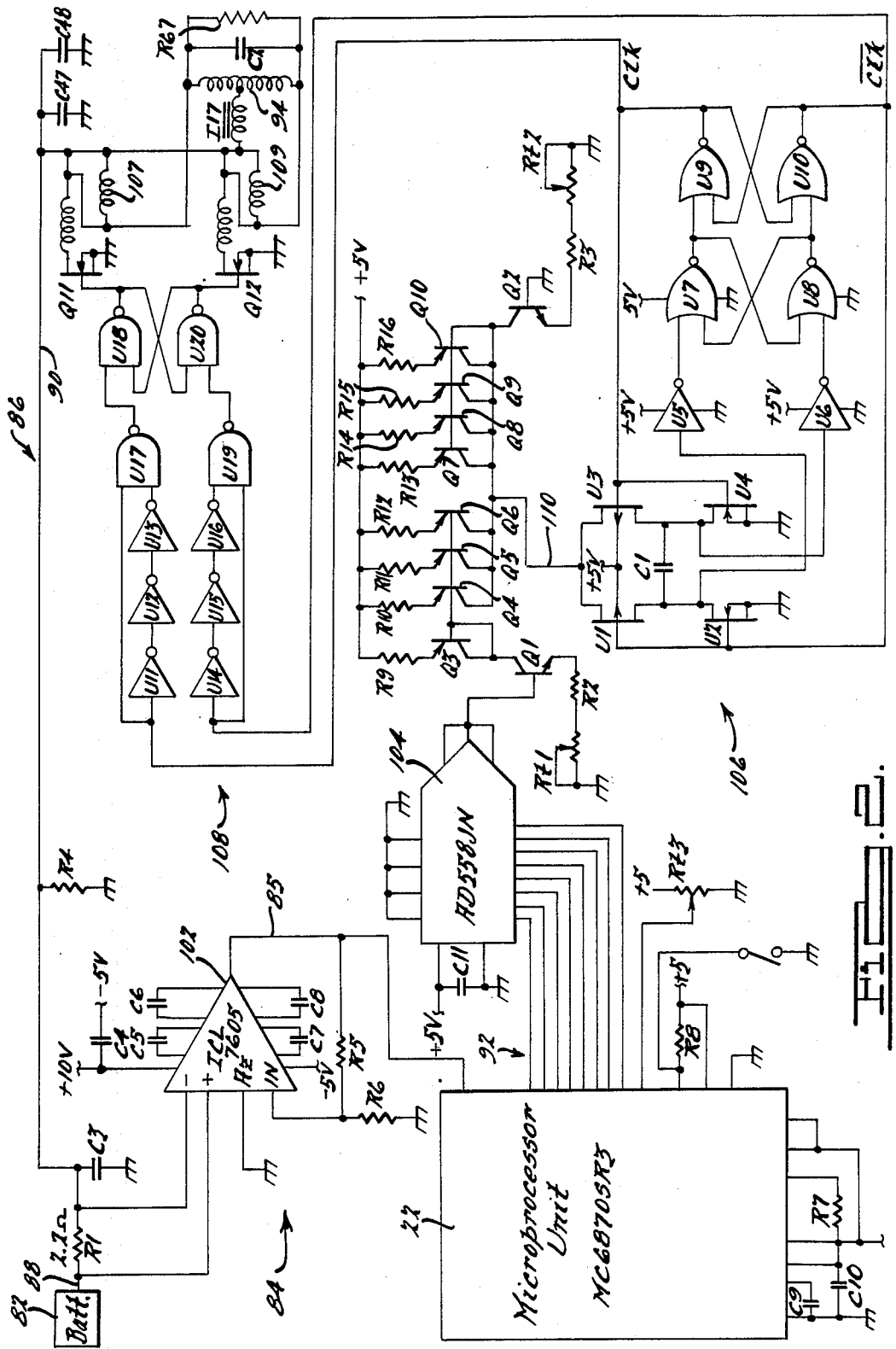
FIG. 2 is a circuit diagram of the power transmitter circuit shown in FIG. 1.

Referring to FIG. 2, a schematic diagram of the power transmitter circuit 86 for the cochlear implant system 10 is shown. Generally, this circuit 86 converts electrical current from the battery 82 into a periodically varying signal, such as a sinusoidal signal, that is transmitted across the cutaneous layer 36 by antenna 94.

While a sinusoidal signal is preferred, it will be appreciated that other types of pulse or periodic signals could be used. It is also preferred that this circuit be a high Q, low bandwidth design to ensure an efficient transmission of electrical power. For example, a bandwidth of 30-50 KHz with a center frequency of 1-2 MHz may be used. This will minimize the current drain on the battery 82.

In one embodiment according to the present invention, power transmission is optimized by adjusting the frequency of the periodically varying power signal until a minimum amount of power is consumed. This is accomplished by adjusting the frequency of the power signal until it matches the resonant frequency of the external antenna 94. The optimization is achieved by a circuit comprising the current sensor 84, the microprocessor 22 and the power transmitter 86. The current sensor 84 includes a resistor R1 which is connected electrically in series with the battery 82. The voltage across the resistor R1 is fed to the input of a differential amplifier 102. The output of the differential amplifier 102 is then fed to the microprocessor 22, which may be, for example, a Motorola 6C8705 or MC68HC11. This microprocessor has an analog to digital converter built into it and could be used for the microprocessor 22 of FIG. 1.

The output of the differential amplifier 102 is converted into a digitized signal by the A/D converter in microprocessor 22. The output from the microprocessor is connected to the power transmitter circuit 86. The power transmitter circuit 86 generally comprises a digital to analog (D to A) converter 104, a voltage controlled oscillator 106 and a pulse generator 108. The output from the power transmitter circuit 86 is connected to the power antenna 94. As a result, the power antenna 94 will oscillate at a predetermined frequency.

The digital output from the microprocessor 22 is connected to the D to A converter 104 in the power transmitter circuit 86. The analog output of the D to A converter 104 is fed to the input of the voltage controlled oscillator 106. It will be appreciated that a voltage controlled oscillator is an oscillator in which the frequency of its output signal is controlled by the voltage of its input signal.

The voltage controlled oscillator circuit 106 generally comprises transistors Q1 and Q1, a pair of current mirrors comprising transistors Q3, Q4, Q5, Q6 and transistors Q7, Q8, Q9 and Q10, CMOS switches U1, U2, U3, and U4, capacitor Cl, a pair of inverters U5 and U6 and NOR gates U7, U8, U9 and U10. The output of the D to A converter 104 is connected to the base of transistor Q1. Thus, transistor Q1 establishes a current which is proportional to the analog output of the D to A converter. The emitter of transistor Q1 is connected to ground through potentiometer Rt1. The upper frequency limit of the voltage controlled oscillator 106 is established by adjusting potentiometer Rt1 which limits the current flow through transistor Q1. This current is then amplified by a current mirror comprising transistors Q3, Q4, Q5 and Q6.

The resulting amplified current is added to a biased current that has been amplified by a second current mirror comprising transistors Q7, Q8, Q9 and Q10. The collector of transistor Q2 is connected to this second current mirror. Potentiometer Rt2 is connected between the emitter of transistor Q2 and ground. Potentiometer Rt2 determines the total current established by the second current mirror. As a result, the minimum frequency of the voltage controlled oscillator 106 can be set by adjusting potentiometer Rt2. Rt1 establishes the maximum frequency.

The current that results from both current mirrors is fed along conductor 110 to a circuit comprising CMOS switches U1, U2, U3 and U4. This circuit directs current into or out of capacitor C1. The level of the resulting discharge on capacitor C1 drives inverters U5 and U6 high or low. The output of these inverters U5 and U6 are connected to a flip flop circuit formed by NOR gates U7, U8, U9 and U10. The output of NOR gates U9 and U10 is connected to the CMOS switches and also to a pulse generator 108 by two conductors labeled clk and $\overline{\text{clk}}$. The clk and $\overline{\text{clk}}$ signals are square waves with a fifty percent duty cycle. Due to the function of the voltage controlled oscillator 106, these signals will have a frequency that is proportional to the analog output of D to A converter 104.

Overall, the optimization of the power transmission is achieved as follows. When the current drain on the battery 82 increases, the voltage across resistor R1 increases. The microprocessor 22 and voltage controlled oscillator 106 then interact to minimize this voltage. At predetermined intervals, the microprocessor 22 will increment the D to A converter 104 which causes the voltage controlled oscillator (VCO) 140 to increase the frequency at which the antenna 94 is oscillating. If, as a result, the power goes up, the microprocessor 22 will sense an increase in the voltage across resistor R1 and decrement the D to A converter 104 and the frequency will be lowered. This will lower the power drain on the battery 82 until the optimum frequency is crossed, at which time the increase in power will cause the microprocessor to increment the D to A converter 104 until the optimum frequency is again reached. A computer program which performs this optimization is set forth in Table I.

As discussed above, the VCO 106 provides output signals labeled clk and $\overline{\text{clk}}$. These signals are then fed to a pulse generator 108 which is comprised of three pairs of inverting amplifiers U11, U12, U13, U14, U15 and U16 and two pairs of NAND gates U17, U18, U19 and U20. These NAND gates are arranged in an RS type flip-flop configuration. This circuit is then connected to two transistors, Q11 and Q12 which may be CMOS type transistors.

The resulting signals out of the flip-flop are short pulses of a duration equal to the delay through the NAND gates. Depending on the state of the NAND gates, one of the two transistors Q11 or Q12 will turn on. These transistors are then coupled to the antenna coil 94. Impedance matching transformers 107 and 109 are connected between transistors Q11 ans Q12 and antenna 94, forming an impedance matching network. The purpose of this network is to match the impedance of the external antenna 94 with the impedance of the internal antenna 76. The DC current from the battery 82 is also fed to the antenna coil 94 along conductor 90 and through an inductor I1. Capacitor C2 is connected across oil 94. The result is that the DC current from the battery 82 is converted into a sinusoidal voltage for transmission to the implant module 14.

Referring now to FIG. 3, a schematic diagram of the power receiver and AC to DC converter circuit 78 for the cochlear implant system 10 is shown. Generally, the AC power signal from antenna coil 94 is transmitted through the cutaneous layer 36 by antenna coil 94. This signal is received by the receiving power antenna coil 76 which is implanted subcutaneously.

Power antenna coil 76 is connected to the power receiver and AC to DC converter circuit 78. This circuit comprises capacitor C12, which is connected across both ends of the antenna coil 76, and transformer 112. Resistor R17 connected across the output of impedance matching network 112. This output feeds an AC to DC converter 113 which is then used to power the rest of the circuits in the implant module 14.

Referring to FIG. 4, a schematic diagram of the information transmitter circuit 28 for the cochlear implant system 10 is shown. In one embodiment according to the present invention, the information transmitter circuit 28 receives multiple channels of digital speech signals from the microprocessor 22 and converts these signals into an amplitude modulated sine wave signal. This signal is then transmitted to the speech signal antenna coil 34.

More particularly, an eight bit digital speech signal is received from the microprocessor 22 by a digital to analog converter 114. As will be appreciated, a digital to analog converter generates an analog output which corresponds to the eight bit command word it receives from the microprocessor 22.

The output of the digital to analog converter 114 is transmitted through an op amp driver U53 to a current adjustment circuit, which includes an emitter follower buffer circuit 118, a Wilson current mirror 120, an decoupling capacitors C13 and C14. The emitter follower buffer circuit 120 comprises transistor Q13, resistors R18 and R19, and potentiometer Rt4. Resistor R19 and potentiometer Rt4 establish the amount of current that will pass ultimately out of the current mirror circuit 120 to a differential transistor pair Q14 and Q15. This current level will then determine the amplitude level that the antenna coil 34 will be driven with.

Current mirror circuit 120 comprises transistors Q16, Q17, Q18 and Q19. This circuit amplified the current coming from the emitter follower circuit 118 by a factor of three. This amplification is advantageous at this point because it prevents excessive drain on the battery which would otherwise occur if the speech signal was amplified during earlier processing.

The voltage source for the current mirror is provided by operational amplifier U51. This voltage is adjusted by potentiometer Rt5. This adjustment ensures that this voltage level matches the characteristics of the digital to analog converter 114 so that the resultant wave forms are symmetric. This circuit establishes the carrier signal.

The amplified speech signal is sent from the current mirror to the differential transistor pair Q14 and Q15 and is then combined with the square wave carrier signal labeled "f carrier". This carrier preferably has a frequency which is not near the power transmission frequency, such as 10 MHz. This is the center frequency of the double side band amplitude modulated signal that is transmitted across the skin. Transistors Q14 and Q15 are alternately switched by this carrier. While each transistor is on, current comes out of the current mirror and flows through the transistor. The resulting speech signal has the form of a square wave current which is then fed to the antenna coil 34.

Capacitors C23 and resistor R17 are connected electrically in parallel with antenna coil 34 forming a tank filter circuit. The purpose of the tank filter circuit is to convert the square wave current signal into a sinusoidal voltage signal. A sinusoidal signal is preferred to reduce the amount of electromagnetic interference that this transmitted signal will emit. In this regard, a 10 MHz square wave will emit more interference because of its higher harmonics than will a 10 MHz sinusoidal wave. The resulting signal is a 10 MHz signal with a relatively wide bandwidth of about 5 MHz. It will be appreciated that other suitable bandwidths may be provided, recognizing that the bandwidth is a function of the number of channels and of the baseband spectrum for each channel.

Figure 5A:
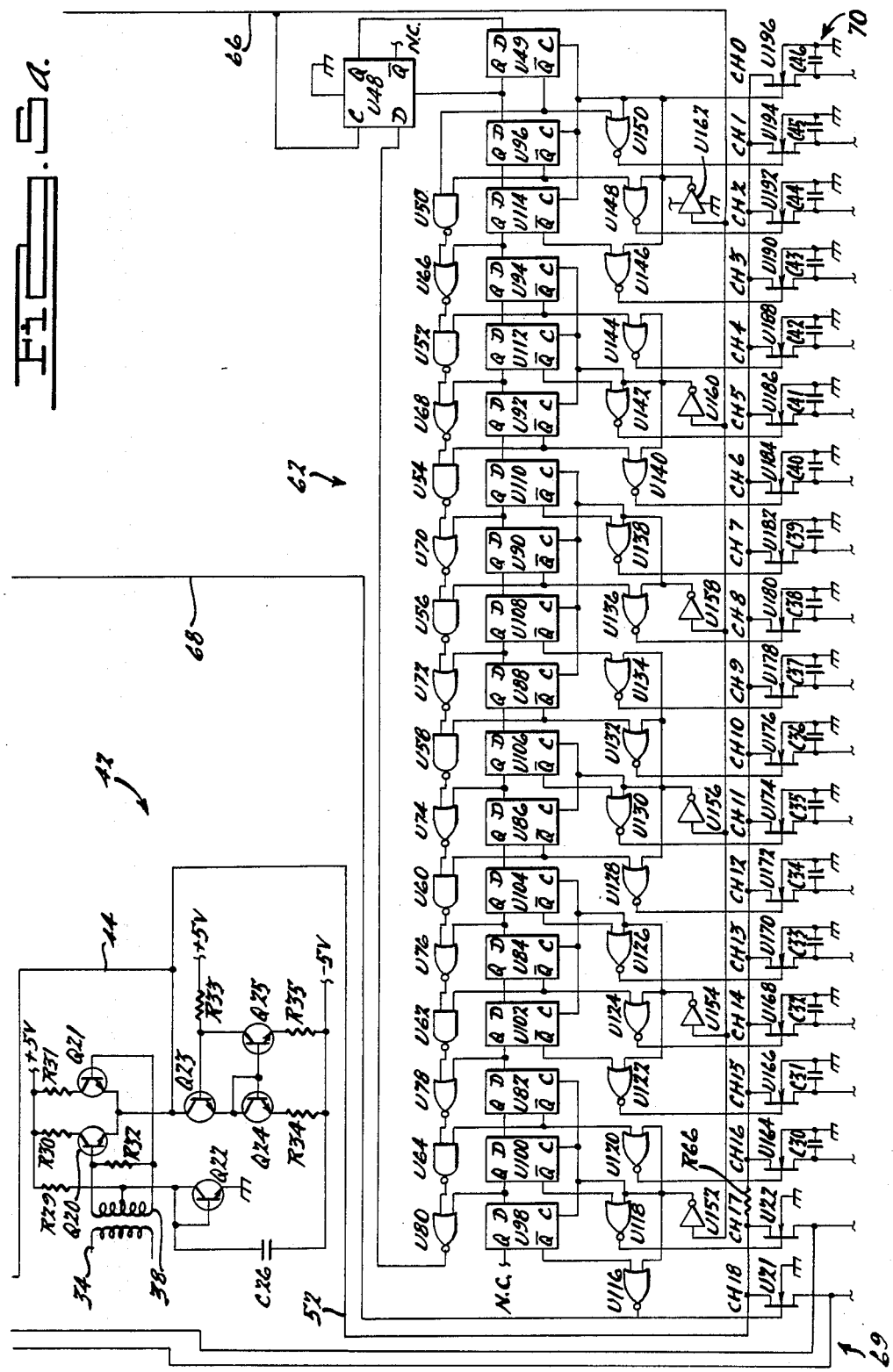
FIG. 5a is a circuit diagram of the envelope detector and 18 stage auto-resettable ring counter shown in FIG. 1.

Referring to FIG. 5a, a schematic diagram of the envelope detector circuit 42 for the cochlear implant system 10 is shown. In general, this circuit demodulates the AM signal that is transmitted across the skin by antenna coil 34 and received by antenna coil 38. In one embodiment according to the present invention, one side of antenna coil 38 is coupled to the base of transistor Q20 while the other side is coupled to the base of transistor Q21. Transistors Q20 and Q21 form a differential pair. During the positive half of this incoming AC speech signal, transistor Q20 turns on and transistor Q21 is off. Thus, transistor Q20 looks like an emitter/follower in that the voltage present at its base is also present at the emitter. The output signal of the envelope detector circuit 42 is transmitted to both the synchronization detector circuit 50, and to the analog switches 70 which are ultimately connected to the electrodes 72. An automatic gain control circuit 46 shown in FIG. 1 may be employed between the envelope detector output and the analog switch to limit the amplitude of the speech signal, and to establish a proper signal level for the sync detector.

During the negative portion of the incoming AC signal, transistor Q21 turns on and transistor Q20 is off, providing a high impedance load. Current from the coil 38 then flows through transistor Q21 and this signal is then transmitted out of the envelope detector. The result is that a fully rectified replication of the transmitted signal is sent to both the synchronization detector circuit 50 and the analog switches 70.

It should be understood that other circuits such as a diode bridge could be used for the envelope detector. However, the advantage of this circuit is that it can handle wideband voltages as low as 15 mv, for example.

Before this rectified speech signal can be used to drive the electrodes, it must be synchronized with the transmitted signal. In this regard, it is important that the synchonization circuits avoid introducing a delay between the actual sync signal and the sync detected output. Such a delay can result in cross-talk between channels. Further, to have an instantaneous sync detection capability would normally require a large amount of current. Such currents are undesirable in an implanted circuit such as this where power consumption should be minimized.

Figure 5B:
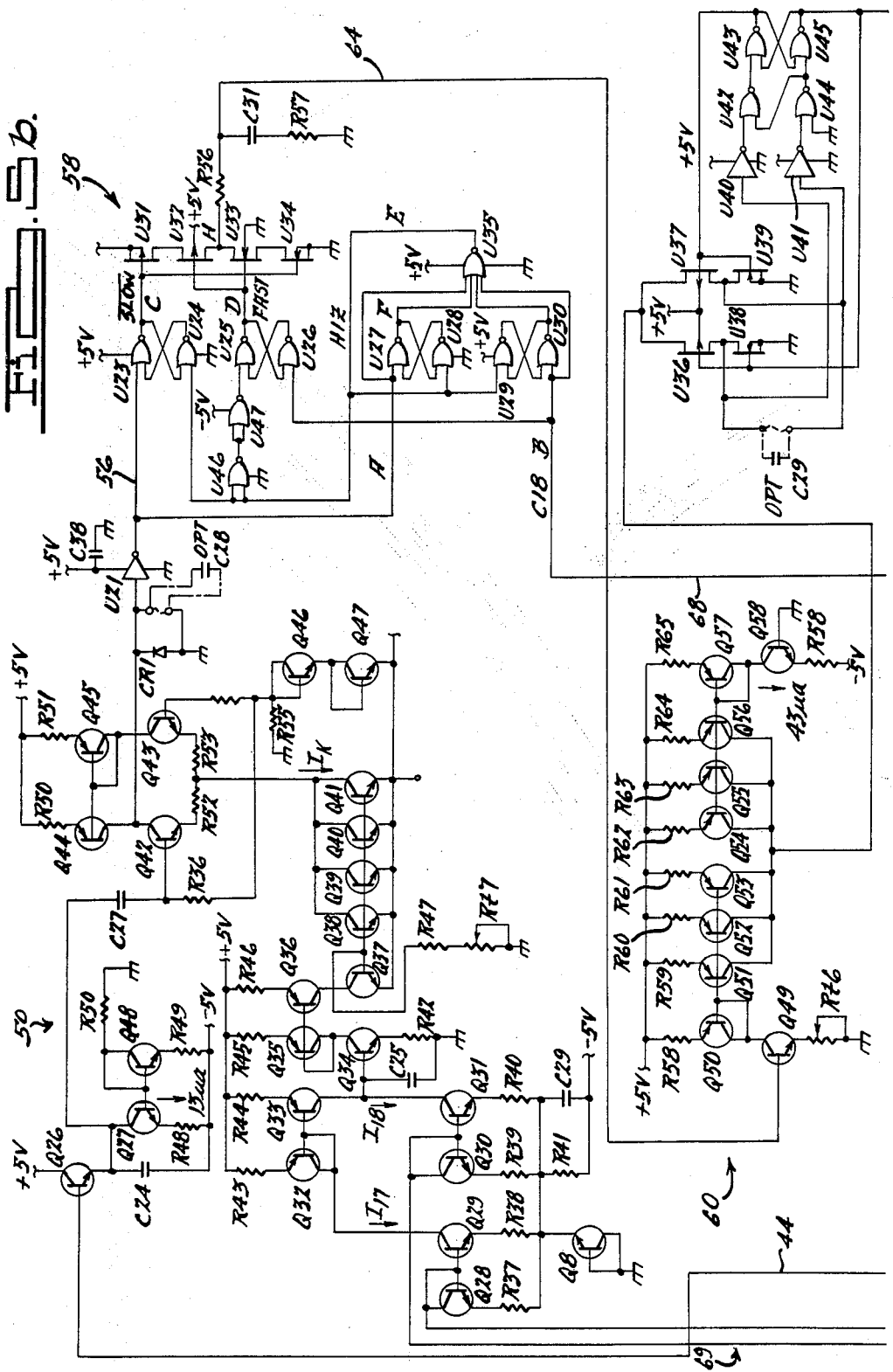
FIG. 5b is a circuit diagram of the synchronization detector, phase comparator and voltage controlled oscillator circuits shown in FIG. 1.

Referring now to both FIGS. 5a and 5b, the synchronization detector circuitry is shown. In one embodiment according to the present invention, this circuit is comprised of the delay network 50, the phase comparator 58, the voltage controlled oscillator 60, and the ring counter 62.

In general, the goal of the sync detector circuit is to detect the sync pulse without a delay and without large currents. The received speech signal is comprised of a number of information channels plus two synchronization channels. The first sixteen channels are information channels and the seventeenth and eighteenth channels contain the sync pulse. The sync pulse begins on the rising edge of the seventeenth clock cycle and continues until the falling edge of the eighteenth clock cycle. The object of this circuit is to use information from the seventeenth and eighteenth clock cycles to determine where the eighteenth clock cycle should actually begin.

The first stage of the sync detector is fed by the speech signal output from the envelope detector 42. The sync detector first determines where the beginning of the synchronization cycle occurs. It then feeds a delay network 50 which squares up the sync detector output and also delays that output according to the proper timing relationships which are determined elsewhere in the circuitry. The sync detector output is a delayed square wave pulse that feeds one of the inputs to the phase comparator 58. The other input to the phase comparator is the eighteenth channel output of the ring counter 62.

This ring counter 62 is an eighteen stage ring counter. The first sixteen channels are used to control the analog switches 70 which feed the recovered audio information to the current drivers. Channels seventeen and eighteen of the ring counter 62 are used to drive analog switches U21 and U22 which feed, by means of conductor pair 69, a balancing network used in the sync detector delay circuit. The eighteenth clock cycle of the ring counter is fed back into the phase comparator 58 on conductor 68. The ring counter 62 is driven by the voltage controlled oscillator 60 through conductor 66. The VCO 60 "walks" the eighteenth clock cycle output of the ring counter 62 to the recovered sync signal. This establishes the proper clock relationship.

In general, the proper synchronization relationship is then determined by the requirement that the integrated output of channel seventeen equals the integrated output of channel eighteen. This relationship is determined by the delay network 50. The delay is determined by the relationship between the recovered sync signal and the recovered clock signal. The feedback is such that a nulling effect will occur and the proper phase delay will result at the sync output.

Figure 6:
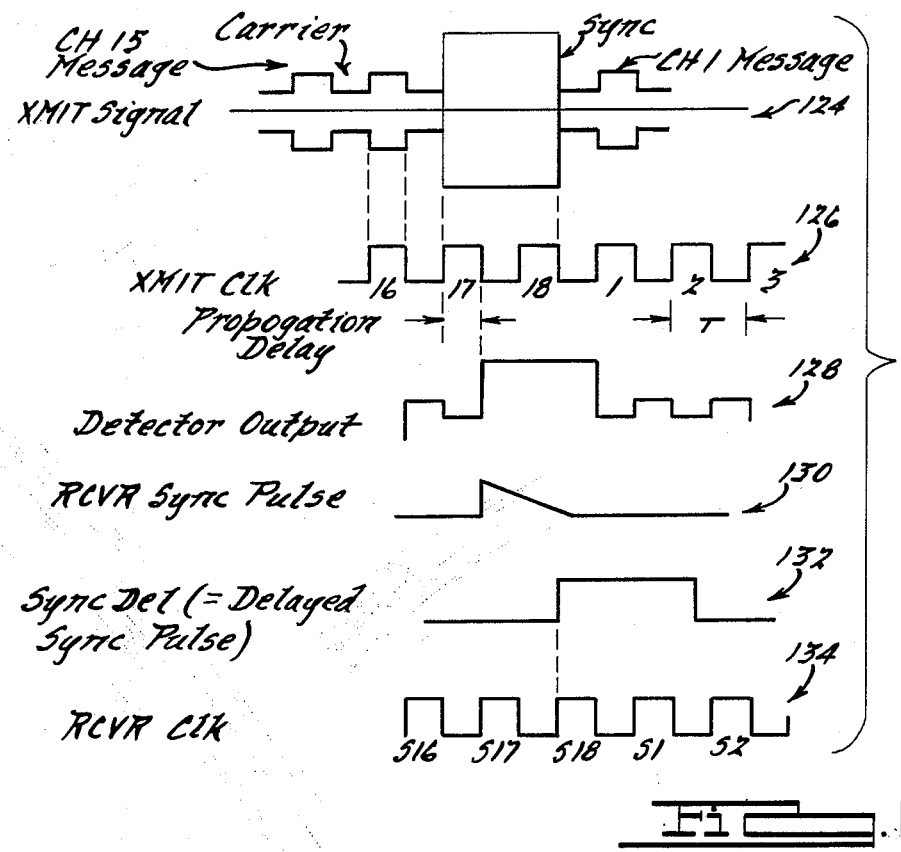
FIG. 6 is a timing diagram of the phase and synchronization detector and delay signals.

Referring now to FIG. 6, a timing diagram of various synchronization signals 124-134 is shown. The transmitted signal 124 includes a synchronization pulse which begins at the leading edge of the seventeenth clock pulse in the clock cycle 126 and lasts until the end of the eighteenth clock pulse. This sync pulse has an amplitude of 200 mv which is preferably set at three hundred percent of the maximum modulation level for the audio information signals. It should be understood that other appropriate ratios could be incorporated, such as a zero amplitude sync pulse.

Referring again to FIG. 5b, the output signal 128 of the envelope detector 42 is fed to the base of transistor Q26 along conductor 44. Capacitor C24 is connected to the emitter of transistor Q26. This forms a peak detector circuit. When the synchronization pulse begins, transistor Q26 turns on and capacitor C24 charges up to the level of the sync pulse. When the sync pulse ends, transistor Q26 will turn off until the next pulse turns it on again. Transistor Q27 functions as a constant current source, and is connected across capacitor C24 to pull current out of capacitor C24 at a constant rate. The resulting linear decreasing current will continue until the next sync signal occurs. The total decrease in the voltage across capacitor C24 will be 200 mv. This results in the saw-tooth wave 130, shown in FIG. 6. The sync signal must be 200 mv greater than the maximum message signal or transistor Q26 will turn on before the next sync pulse.

This saw-tooth wave is then converted into a square wave by the delay network 50. The sync detection output is also delayed according to the proper timing relationships determined by the delay network. The purpose of the delay network 50 is to establish the proper synchronization relationships of the overall circuit. The delay network 50 does this by requiring that the integrated output of analog channel seventeen is equal to the integrated output of channel eighteen. This occurance can only exist if the exact timing relationships exist between the recovered seventeenth and eighteenth clock cycles and the signal coming out of the envelope detector.

Referring to FIGS. 5a and 5b, analog switch U22 is switched on during the seventeenth recovered clock cycle. This allows the envelope detector output to flow through conductor 52 to analog switch U22 and then through conductor pair 69 to the bases of transistors Q28 and Q29 in the delay network 50. In a similar fashion during the eighteenth recovered clock half cycle, analog switch U21 is turned on and the envelope detector output is fed along conductor 69 pair to the bases of transistors Q30 and Q31.

Thus, during the seventeenth clock half cycle, transistor Q28 is turned on and a current labeled $I_{17}$ flows through transistor Q29. Also current $I_{17}$ is current mirrored through transistors Q32 and Q33. This results in a charge on capacitor C25. During this time, current $I_{18}$ is zero because analog switch U21 is off and no current is flowing to transistors Q30 and Q31.

During the recovered eighteenth clock half cycle transistors Q30 and Q31 are being fed the information from the envelope detector. A current proportional to that voltage is mirrored into transistor Q31. Now, transistor Q29 will have zero current flowing through it because there is no voltage being supplied to transistor Q28. Current $I_{18}$ will then be fed from capacitor C25 discharging this capacitor.

The result of this signal cycling during the recovered clock cycles seventeen and eighteen, is that capacitor C25 is charged and discharged with a net voltage that is proportional to the imbalance of the circuit. This imbalance is proportional to the skew between the recovered seventeenth and eighteenth clock cycles and the envelope detector's synchronization cycle. This net voltage on capacitor C25 is then used to establish a current through transistor Q34. This current is then mirrored through transistor Q35 and Q36 and down into transistor Q37. Transistor Q37 is then current mirrored through transistors Q38, Q39, Q40, Q41 and fed into the emitter lines of transistors Q42 and Q43.

Therefore, the current labeled $I_k$ is proportional to the imbalance between the seventeenth and eighteenth recovered clock cycles and the envelope detector's sync signal levels. Eventually $I_k$ will adjust the amount of speech signal delay through transistors Q44, Q45, Q42 and Q43 which will result in a delay of the square wave pulse out of inverter 421. This pulse is labeled 132 in FIG. 6.

As discussed above in connection with the sync detector circuit, the sync signal, which looks like a sawtoothed wave form, is fed from the sync detector circuit into transistors Q42 and Q43. The positive edge of this waveform occurs at the beginning of the sync signal and the ramp portion lasts the entire length of time between successive sync signals. This waveform is labeled 130 on FIG. 6. Transistors Q42 and Q43 are equally biased by transistors Q46 and Q47 so that approximately equal levels of current are fed through transistors Q42 and Q43 when no sync signal is present.

Capacitor C27, in conjunction with resistor R36 serves as a high pass filter to create a pulse instead of a saw-toothed wave form at the base of transistor Q42. That pulse will turn transistor Q42 on and transistor Q43 off. Current $I_k$ will be proportional to the phase skew between channels seventeen and eighteen.

Since there is no current through transistor Q43, there is no current through transistors Q44 and Q45, and all the current through transistor Q42 is used to discharge capacitor C28. This capacitor is labeled optional because it is possible that the parasitic capacitance of inverter U21 can serve as that capacitance level. When the voltage across capacitor C28 goes below a defined threshold level of inverter U21, the inverter output turns on. When the sync pulse goes away, transistor Q43 turns on and current $I_k$ is routed through transistors Q43 and Q45 which is then current mirrored into transistor Q44. This will have the effect of charging capacitor C28 back up.

It should be noted that the important aspect of this circuit is the turn-on time of inverter U21, not the turn-off time. Only the positive edge of the inverter U21 output waveform is used. The result is a signal that is detected at the beginning of the sync signal and is delayed a proportional amount as determined by the phase delay network. As described above, this delay is based upon the relationship between the recovered sync signal and recovered clock signals seventeen and eighteen. Thus, the feedback is such that a nulling effect will occur and the proper phase delay will result at the sync output.

Figure 7:
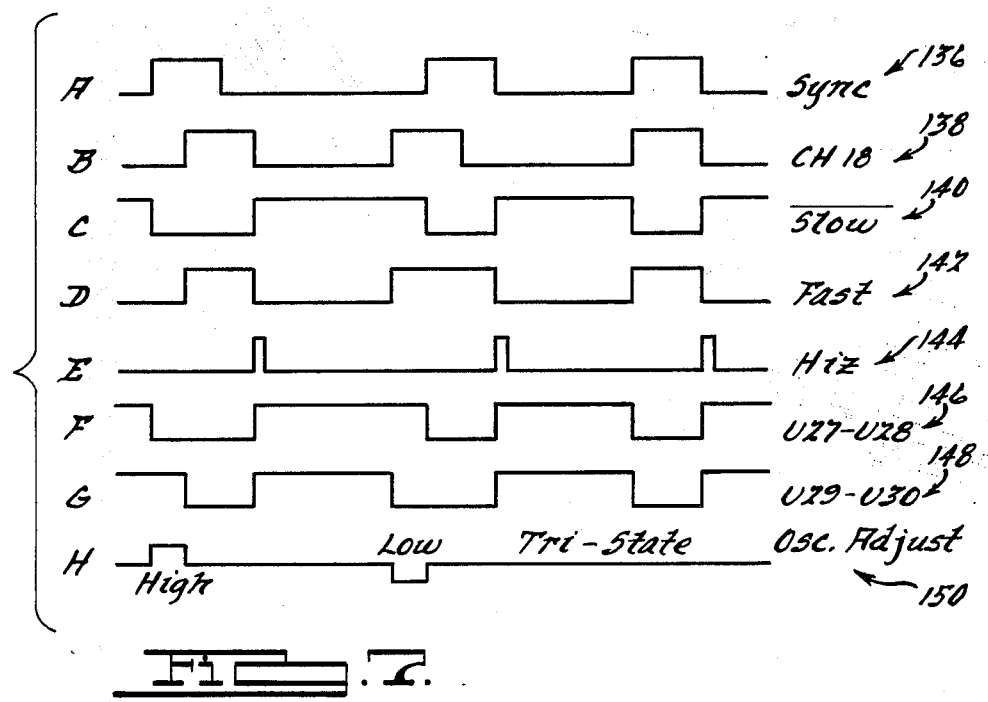
FIG. 7 is a timing diagram of the phase comparator and synchronization detector signals.

This delayed pulse is fed into the phase comparator 58 by conductor 56. The eighteenth clock cycle of the ring counter 62 is also fed into this circuit through conductor 68. In general, the phase comparator compares these two pulses to determine whether or not the clock is running too fast or too slow or is just right. Referring to FIG. 7, if the channel eighteen clock cycle 138 is too slow compared to the sync signal 136, the slow signal 140 will be in the low state for longer than the sync cycle and capacitor C31 will become charged. If the channel eighteen clock is too fast, the fast signal will be in the high state for longer than the sync pulse and capacitor C31 will be discharged. If the timing is equal, both slow and fast signals are on only during the sync pulse and capacitor C31 is not charged or discharged. The resultant charge on capacitor C31 determines the actual oscillator frequency of the voltage controlled oscillator 60. Thus, when the eighteenth clock cycle is slow, capacitor C31 is charged, the voltage at the input to the voltage control oscillator is higher, and the frequency is increased. When the clock is fast, capacitor C31 is discharged, the voltage going into the voltage controlled oscillator 60 is decreased and the frequency is decreased.

It should be appreciated that various types of phase comparators may be used. However, in one embodiment according to the present invention a phase comparator 58 employs NOR gates U23, U24, U25, U26, U26, U28, U29 and U30 in a flip-flop configuration to produce the slow and fast signals.

Referring again to FIG. 5b, the voltage controlled oscillator 60 is shown. The voltage controlled oscillator circuit 60 will respond to the voltage level of the input signal from the phase comparator 58 to vary the frequency of its output signal. In one embodiment according to the present invention, the voltage controlled oscillator circuit 60 includes transistor Q49 which is connected at is base to the phase comparator 58 by conductor 64. Transistor Q49 establishes a current proportional to the phase error voltage on capacitor C31. That current is then amplified by a current mirror consisting of transistors Q50, Q51, Q52 and Q53.

The resulting current is added to a biased current that has been amplified by a second current mirror comprising transistors Q54, Q55, Q56 and Q57. Resistor R58 is connected between the emitter of transistor Q58 and a nominal five volt supply. The collector of transistor Q58 is connected to the collector of transistor Q57. The value of resistor R58 will thus determine the total current established by transistors Q54, Q55, Q56 and Q57. This, in turn, will determine the minimum frequency of the voltage controlled oscillator 60.

Likewise, potentiometer Rt6 will determine the amount of current flowing though transistor Q49 and will establish the upper frequency of the VCO 60. In this embodiment of the invention, resistor R58 and potentiometer Rt6 may be laser trimmed to establish these limits. The resulting current is then routed to a circuit comprising CMOS switches U36, U37, U38 and U39. This circuit is switched on to steer current into or out of optional capacitor C29. Capacitor C29 is optional because in this embodiment of the invention CMOS circuits are used and the inherent parasitic capacitance of this circuit performs the function of capacitor C29. If, for instance, high speed CMOS circuits were employed, instead of 4000 Series CMOS circuits, an actual capacitor would be used for capacitor C29. In the embodiment shown, each of the analog switches are preferably MC14007 CMOS switches.

It is the level of the resulting discharge on capacitor C29 which drives inverters U40 and U41 high or low. NOR gates U42, U43, U44 and U45, in a flip-flop arrangement are connected to the output of inverters U40 and U41. The effect of the flop-flop circuit will be to lock a particular phase of the recovered clock and to feed that signal back to the CMOS switches U36, U37, U38, U39. The output of NOR gate U45 is then fed to the ring counter 60 through conductor 66.

Referring to FIG. 5a, ring counter 62 is shown. This is an eighteen stage ring counter that is used as a down counter for the phase comparator network 58. It is also used for driving the analog switches 70. As will be appreciated, a ring counter is a serial shift register whose output is fed back into the input.

In this embodiment of the invention, ring counter 62 includes a flip-flop circuit U48 which is fed by the output of the voltage controlled oscillator 60. The output of flip-flop U48 feeds the D input to a flip-flop U49 which in turn feeds one input of NAND gate U50. NAND gate U50 is part of a series of alternating NAND gates U50–464 and NOR gates U66–U80. In this arrangement, the output of each NAND and NOR gate feeds one of the inputs to the next gate. One input of the NAND gates is connected to the Q output of one of a series of flip-flops U82–U96. Similarly, the inputs to the NOR gates are connected to the D inputs of flip-flops U98, U82–U94 and also to the Q output of flip-flops U100–U114.

The Q output of each of the flip-flops U82–U114 feeds one input to a series of NOR gates U116–U150. The other input to each of these NOR gates is fed by the voltage controlled oscillator output signal through inverters U152–U162. In this embodiment, each of the flip-flops U82–U114 are MC14013 flip-flops.

Analog switches 70 are coupled by conductor 52 to the recovered audio signal coming from the envelope detector 42. Except for analog switches U21 and U22, the output of each of the above NOR gates feed the input gate of one of the corresponding analog switches U164 to U196. Each of these analog switches 70 is also connected to one of the current drivers 74 with capacitors C30 to C46 connected between this output and ground. Analog switches U22 and U21 respond to channels seventeen and eighteen and do not drive electrodes. Switch U21 is switched by the eighteenth ring counter cycle which is also coupled to the phase comparator 58. The output of switch U21 which contains the sync pulse, is then sent to the delay network 50 along conductor pair 69. Similarly, switch U22 is switched by the seventeenth ring counter cycle and its output is also sent to the delay network along conductor pair 69. Resistor R66 causes a slight delay (nanoseconds) in the signal to ensure that U22 and U21 turn off before the analog signal goes away.

The current drivers 74 receive electrical power from the power receiver and AC to DC converter circuit 78 and also from the rest of the receiver circuitry. Each of these current drivers are also coupled to one of the electrodes 72.

In summary, as a result of the precise control over the timing of the audio signals achieved by the above circuitry, each analog switch 70 is turned on at the precise time the audio signal in the corresponding channel is being sent on conductor 52. In this way, only the electrode coupled to the correct analog switch receives the audio signal for the appropriate channel.

In accordance with the embodiment of the present invention, a computer program for the microprocessor 22 is set forth below in Table I. This program provides one set of exemplary computer instructions for optimizing the efficiency of the transcutaneous power transmission.

It will be appreciated that the above disclosed embodiment is well calculated to achieve the aforementioned objectives of the present invention. In addition, it is evident that those skilled in the art, once given the benefit of the foregoing disclosure may now make modifications of this specific embodiment described herein without departing from the spirit of the present invention. Such modifications are to be considered within the scope of the present invention, which is limited solely by the scope and spirit of the appended claims.

TABLE I

| | | Global Equates: | |
|---|---|---|---|
| MIMSIZ | EQU | $1000 | Memory Address space size |
| PORTA | EQU | $000 | I/O port locations: |
| DA | SET | PORTA | |
| PORTB | EQU | $001 | |
| PORTC | EQU | $002 | |
| PORTD | EQU | $003 | |
| DDR | EQU | 4 | offset from port base location for DDRs |
| TIMER | EQU | $008 | B-bit timer register |
| TDR | SET | TIMER | |
| TCR | EQU | $009 | timer control register |
| MISC | EQU | $00A | miscellaneous register |
| EPC | EQU | $00B | programming control register (no user access) |
| ADCSR | EQU | $00E | A/D control and status register |
| ADATA | EQU | $00F | A/D result register |
| RAM | EQU | $010 | start of user RAM |
| INITSP | EQU | $07F | SP after RSP |
| ZROM | EQU | $080 | start of base page EPROM |
| ROM | EQU | $100 | start of main EPROM |
| ENDROM | EQU | $F37 | last byte of user EPROM |
| MOR | EQU | $F38 | Mask Option Register (no user access) |
| MORT | EQU | $80 | Option Code Register setup |
| | | Bits of various registers: | |
| EOC | EQU | 7 | end of A/D conversion bit in ADCSR |
| B0 | EQU | 0 | PORTB BIT 0 |
| B1 | EQU | 1 | PORTB BIT 1 |
| B2 | EQU | 2 | PORTB BIT 2 |
| B3 | EQU | 3 | PORTB BIT 3 |
| | | Global variables on page zero: | |
| MODE | EQU | 6 | MODE SELECT |
| Note: Common PSCT used so that each module shares this. "CONSTS" is just a name for this section... | | | |
| CONSTS | COMM | PSCT | |
| CENTER | FCB | $7F | VALUE TO CENTER D TO A CONVERTER |
| Note: common dsct used so that each module shares this. "DATA" is just a name for this section... | | | |
| DATA | COMM | DSCT | |
| TEMP | RMB | 1 | TEMPORARY HOLDING REGISTER |
| FLIP | RMB | 1 | REGISTER TELLS WHICH DIRECTION (INC. OR DEC.) |
| | PSCT | | |
| | | NAM    CECRST | MULTI-CHANNEL COCHLEAR SUBROUTINE |
| | | ********** CECRST | This routine is the reset and set up for all PORTS. Also it will do a set up routine when mode is selected at reset.*********** |

TABLE I-continued

| | | | | | | |
|---|---|---|---|---|---|---|
| 8 | | | | | | |
| 9 | | | | | | |
| 10 | | | | | | |
| 11 | | | | | | |
| 12 | | | | XDEF | RESET | ROUTINE FOR RESET |
| 13 | | | | XREF | MAIN | MAIN PROGRAM LOOP |
| 14 | | | | | | |
| 15 0000 P | 9B | | RESET | SEI | | MASK INTERRUPT |
| 16 0001 P | 1C | 0A | | BSET | 6,MISC | MASK INT2 IN MISC. REQ. |
| 17 0003 P | 1C | 09 | | BSET | 6,TCR | MASK TIMER INTERRUPT IN TCR |
| 18 0005 P | A6 | FF | | LDA | #$FF | LOAD ACCA. WITH ALL 1'S |
| 19 0007 P | B7 | 04 | | STA | PORTA+DDR | SETTING UP PORTA FOR DATA BUSS (OUTPUTS) |
| 20 0009 P | B7 | 05 | | STA | PORTB+DDR | SETTING UP PORTB FOR TEST POINT (OUTPUTS) |
| 21 0011 P | 3F | 06 | | CLR | PORTC+DDR | SETTING UP PORTC FOR INPUTS ONLY |
| 22 | | | | | | |
| 23 000D P | C6 | 00000 | | LDA | CENTER | LOAD VALUE OF CENTER FOR D/A |
| 24 0010 P | B7 | 00 | | STA | DA | PUT CENTER VALUE ON DATA BUSS. |
| 25 0012 P | 0C | 03 | 06 SETUP | BRSET | MODE,PRDTD,READ | BRANCH IF BIT 6 OF PORTD IS HIGH. |
| 26 0015 P | 10 | 01 | | BSET | B0,PORTB | TEST POINT. |
| 27 0017 P | 11 | 01 | | BCLR | B0,PORTB | TEST POINT. |
| 28 0019 P | 20 | F7 | | BRA | SETUP | BRANCH BACK TO SETUP |
| 29 | | | READ | CLR | ADCSR | CLEAR A/D CONTROL REGISTER. (STARTS A CONV.) |
| 30 001B P | 3F | 0E | | | | |
| 31 001D P | 12 | 01 | LOOP | BSET | B1,PORTB | TEST POINT |
| 32 001F P | 13 | 01 | | BCLR | B1,PORTB | TEST POINT |
| 33 0021 P | 0F | 0E | 09 | BRCLR | EOC,ADCSR,LOOP | WAITING FOR END OF CONVERSION. |
| 34 0024 P | B6 | 0F | | LDA | ADATA | LOAD ACCA. WITH VALUE OF CONVERSION. |
| 35 0026 P | C7 | 0000' | | STA | TEMP | TEMPORARY HOLDING REGISTER |
| 36 0029 P | CC | 0000x | | JMP | MAIN | JUMP TO MAIN PROGRAM LOOP. |
| 37 | | | | | | |
| 38 | | | | END | | |
| 2 | | | | NAM | CECVEC | MULTI-CHANNEL COCHLEAR VECTOR ROUTINE |
| 3 | | | | | | |
| 4 | | | | ************************************************************* | | |
| 5 | | | | | | |
| 6 | | | | XREF | RESET | STARTING OF PROGRAM (RESET ROUTINE) |
| 7 | | | | XREF | INT | INTERRUPT SERVICE ROUTINE |
| 8 | | | | XREF | TINT | TIMER INTERRUPT SERVICE ROUTINE |
| 9 | | | | XREF | SWISRV | SOFTWARE INTERRUPT SERVICE ROUTINE |
| 10 | | | | | | |
| 11 | 0FF8 | | | ORG | MEMSIZ-B | START ROM AT LOCATION 80 |
| 12 | | | | | | |
| 13 0FF8 A | 0000X | | TVEC | FDB | TINT | SAME AS ABOVE |
| 14 0FFA A | 0000X | | IVEC | FDB | INT | SAME AS ABOVE |
| 15 0FFB A | 0000X | | SVEC | FDB | SWISRV | SAME AS ABOVE |
| 16 0FFC A | 0000X | | RVEC | FDB | RESET | SAME AS ABOVE |
| 17 | | | | | | |
| 18 | 0F38 | | | ORG | | MASK OPTION REGISTER |
| 19 | | | | | | |
| 20 0F38 A | 80 | | MVEC | FCB | MOPT | OPTION CODE REGISTER |
| 21 | | | | | | |
| 22 | | | | END | | |

MICROBENCH 6805 LINKER (IV)     LOAD MAP
CECFOO. LDA
\*\*\* ABSOLUTE SEGMENT \*\*\*

| | | | | | |
|---|---|---|---|---|---|
| ASCT | ADDR: | 0000 | SIZE: | 1000 | MODULE: |

\*\*\* BASE SEGMENTS \*\*\*

| | | | | | |
|---|---|---|---|---|---|
| CSCT | ADDR: | 0010 | SIZE: | 0000 | MODULE: |
| DATA | ADDR: | 0010 | SIZE: | 0002 | MODULE: CECRST |

\*\*\* ROM SEGMENTS \*\*\*

| | | | | | |
|---|---|---|---|---|---|
| CONSTS | ADDR: | 0080 | SIZE: | 0001 | MODULE: CECRST |
| PSCT | ADDR: | 0081 | SIZE: | 002C | MODULE: CECRST |
| | RESET: | 0081 | | | |
| PSCT | ADDR: | 00AD | SIZE: | 0079 | MODULE: CECMAN |
| | INT: | 00F5 | MAIN | 00AD | SWISRV 00F4 TINT 00F3 |
| PSCT | ADDR: | 0216 | SIZE: | 0000 | MODULE: CECVEC |

TRANSFER ADDRESS = 0000
HIGH BASE ADDRESS = 0000
HIGH RAM ADDRESS = 0012
HIGH ROM ADDRESS = 0126
MEMORY = 1000

We claim:
1. A system for electrically stimulating sensory nerves via electrically powered stimulating electrodes, the system comprising:

means for generating a plurality of channels of electrical information in response to an external stimulus;

means for transmitting said plurality of channels of electrical information across a first single wireless transcutaneous path, said means for transmitting including means for combining said plurality of channels of electrical information into a single wide bandwidth amplitude modulated ("AM") signal containing said plurality of channels of electrical information for transmission across said transcutaneous path;

means for receiving said single wide bandwidth AM signal containing said plurality of channels of electrical information transmitted across the single transcutaneous path;

means for recovering from said received wide bandwidth AM signal said plurality of channels of electrical information contained therein;

means for distributing said recovered plurality of channels of electrical information to a plurality of stimulating electrodes in a predetermined sequence in time;

means for generating a periodically varying narrow bandwidth signal distinct from said wide bandwidth AM signal;

means for transmitting electrical power via the periodically varying narrow bandwidth signal across a second single wireless transcutaneous path;

means for receiving said periodically varying signal transmitted across said second transcutaneous path to obtain said transmitted electrical power; and means for coupling said obtained electrical power to said means for recovering and said means for distributing, whereby said means for recovering and said means for distributing can operate without an implanted battery.

2. The system according to claim 1, wherein said sensory nerves are auditory nerves, said external stimulus is audible sound, and each of said channels of electrical information contains audio information derived from said audible sound.

3. The system according to claim 2, wherein the means for generating includes:
means for converting said external sound into an electrical information signal;
means for separating said electrical information signal into a predetermined number of said channels of electrical information, each said channel comprising a predetermined portion of said electrical information signal; and
means for programmably altering the content of the portion of the electrical information signal in each said channel, said means for programmably altering including a digital signal processing means.

4. The system according to claim 2 wherein said wide bandwidth amplitude modulated signal is a double side band modulated sine wave signal having a nominal frequency approximately twice its band width, said normal frequency being in the Megahertz range.

5. The system according to claim 2, where said modulated signal has a nominal frequency of 10 MHz and a bandwidth of about 5 MHz.

6. The system according to claim 1, where said means for receiving said wide bandwidth AM signal includes means for synchronizing said wide bandwidth AM signal with said means for transmitting said plurality of channels of electrical information.

7. The system according to claim 1, where said means for distributing includes switching means for directing respective ones of said recovered plurality of channels of electrical information to respective ones of said plurality of stimulating electrodes at times that are appropriate for each channel of said electrical information that is being transmitted, said switching means including a plurality of analog switches, with one such analog switch being provided for each channel of electrical information.

8. The system according to claim 1 further including means for sensing an amount of power transmitted across both single wireless transcutaneous paths and means for adjusting the frequency of the periodically varying signal in response to the amount of power sensed by said means for sensing such that the efficiency of the power transmission is optimized.

9. The system according to claim 1, where said periodically varying signal is a sinusoidal signal.

10. A system for supplying information and electrical power to an implanted medical device, the system comprising:
means for transmitting information to the implanted device over a first wireless transcutaneous path, said means for transmitting including means for generating a wide bandwidth signal carrying the information to be transmitted across said path;
means, forming part of the implanted device, for receiving the transmitted wide bandwidth signal;
means for generating a periodically varying narrow bandwidth signal from an external power source, said narrow bandwidth signal having a bandwidth of about at least an order of magnitude less than said wide bandwidth signal;
means for transmitting said periodically varying narrow bandwidth signal across a second wireless transcutaneous path;
means for receiving said periodically varying signal across the second wireless transcutaneous path; and
means for coupling said electrical power from said receiving means to said implanted device, whereby said implanted medical device can operate without an implanted battery.

11. The system according to claim 10, further including means for sensing the amount of power transmitted, and means for adjusting the frequency of the AC signal whereby the efficiency of the power transmission is periodically optimized.

12. The system according to claim 10, where said periodically varying signal has a bandwidth in the range from about 30 KHz to 50 KHz, and a center frequency in the range of about 1 MHz to about 2 MHz.

13. A method of supplying electrical power to an implanted cochlear device, comprising the steps of:
generating a periodically varying signal of nominal frequency from an external self-contained electrical power source;
transmitting said periodically varying signal across a single wireless transcutaneous path to the implanted cochlear device;
automatically and substantially continuously sensing the amount of electrical power being drawn from the electrical power source;
automatically and substantially continuously adjusting the frequency of the periodically varying signal until a minimum amount of electrical power is drawn from the self-contained power source;
receiving said periodically varying signal across the single wireless transcutaneous path; and coupling said received periodically varying signal to said implanted device, whereby said implanted cochlear device can operated without an implanted battery, and the efficiency of the power usage from the power source is substantially continuously optimized.

14. The method according to claim 13, wherein the self-contained electrical power source is a battery, and the step of sensing includes detecting the current flowing from the battery, and the step of adjusting includes using a microprocessor to determine the adjustment if any to be made to the frequency of the periodically varying signal.

15. A method of providing multi-channel information to implanted electrically operated stimulating electrodes for electrically stimulating sensory nerves, the method comprising the steps of:
generating a plurality of channels of electrical information in response to an external stimulus using a speech processor;
digitizing the electrical information for presentation to a microprocessor;
using the microprocessor to direct the operation of the speech processor;
converting digital information from the microprocessor to a wide bandwidth analog signal including clock and synchronization pulses and information from said plurality of said channels of electrical information,
transmitting said wide bandwidth analog signal including said clock and synchronization pulses and information from said plurality of channels of electrical information across a single transcutaneous path;
receiving said wide bandwidth analog signal transmitted across the single transcutaneous path;
recovering from said received wide bandwidth analog signal said information from said plurality of channels of electrical information by among other things detecting said synchronization and clock pulses in the received analog signal; and
distributing said plurality of channels of electrical information to a plurality of stimulating electrodes in a predetermined sequence in time.

16. The method according to claim 15, where said sensory nerves are auditory nerves, said external stimulus is audible sound, and each of said channels of electrical information contains audio information derived from said audible sound.

17. The method according to claim 16, including the steps of converting said external sound into an analog electrical signal, and separating said electrical signal into a predetermined number of channels each comprising a predetermined portion of said audio signal using said speech processor.

18. The method according to claim 16, wherein said step of distributing includes the successively performed substeps of respectively directing each said received channel of electrical information to a corresponding one of said stimulating electrodes at a distinct interval of time that is allocated for each said respective channel of said electrical information that is transmitted.

19. The method according to claim 18, further including the step of modulating the amplitude of said received wide bandwidth signal prior to the distributing step.

20. The method according to claim 18, wherein said recovering step includes the substeps of:
rectifying said wide bandwidth analog signal; and
synchronizing said received rectified signal with said transmitted signal.

21. A system for electrically stimulating sensory nerves via electrically powered stimulating electrodes, the system comprising:
means for generating a plurality of channels of electrical information in response to an external stimulus;
means for transmitting said plurality of channels of electrical information across a first single wireless transcutaneous path, said means for transmitting including means for combining said plurality of channels of electrical information into a single amplitude modulated ("AM") signal containing said plurality of channels of electrical information for transmission across said transcutaneous path;
means for receiving said single wide bandwidth AM signal containing said plurality of channels of electrical information transmitted across the single transcutaneous path;
means for recovering from said wide bandwidth AM signal, said plurality of channels of electrical information contained therein; and
means for distributing said recovered plurality of channels of electrical information to a plurality of stimulating electrodes in a predetermined sequence, and wherein
said single AM signal includes a synchronization pulse, and
said means for decoding further includes means for detecting said synchronization pulse as part of recovering said plurality of channels of electrical information.

22. The system according to claim 21, where said means for detecting said synchronization pulse includes a delay network circuit, a phase comparator circuit, a voltage controlled oscillator circuit and a ring counter circuit.

* * * * *

UNITED STATES PATENT AND TRADEMARK OFFICE
CERTIFICATE OF CORRECTION

PATENT NO. : 4,918,745
DATED : April 17, 1990
INVENTOR(S) : Steve Hutchinson

It is certified that error appears in the above-identified patent and that said Letters Patent is hereby corrected as shown below:

Column 1, Line 21            "sould"
should be --sound--.

Column 1, Line 65            "protions"
should be --portions--.

Column 1, Line 66
"stimulate" should be --simulate--.

Column 6, Line 53            "detects"
should be --directs--.

Column 7, Line 46            "Q1 and
Q1" should be --Q1 and Q2--.

Signed and Sealed this

First Day of October, 1991

Attest:

HARRY F. MANBECK, JR.

*Attesting Officer*        *Commissioner of Patents and Trademarks*